Aug. 10, 1971 A. M. COCKER Plant Pat. 3,056
ROSE PLANT
Filed Sept. 4, 1969
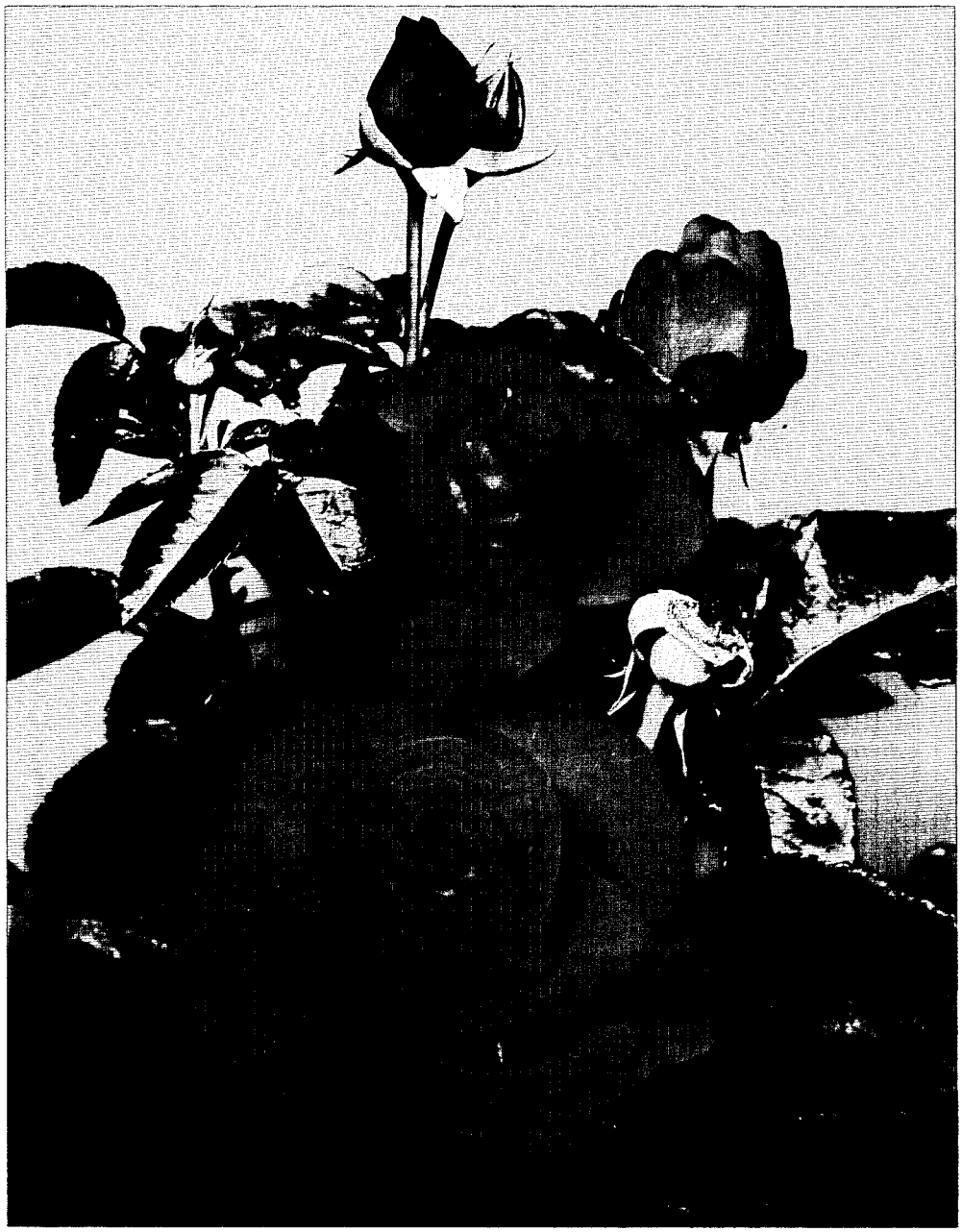
Alexander Morrison Cocker
By
Burns, Doane, Benedict, Swecker & Mathis
Attorneys

United States Patent Office

Plant Pat. 3,056
Patented Aug. 10, 1971

3,056
ROSE PLANT

Alexander Morrison Cocker, Whitemyres, Lang Stracht, Aberdeen, Scotland

Filed Sept. 4, 1969, Ser. No. 855,433
Int. Cl. A01h *5/00*
U.S. Cl. Plt.—20 1 Claim The present invention relates to a new and distinct Rose Plant of the hybrid tea class which was originated by me by crossing the variety Fragrant Cloud (Plant Patent No. 2,574 with the variety Dame de Coeur.

This rose differs from its seed parent Fragrant Cloud by its red color, taller, more vigorous growth, bloom has more petals, and it does not fade purple as much as Fragrant Cloud.

As compared to its pollen parent Dame de Coeur, the bloom is quite different by having a deeper color, more petals, better flower form, strong fragrance and more free-flowering.

As a result of this breeding, I have produced a new rose variety which is distinctly different from both of its parents, as well as all other varieties of its class of which I am aware.

Asexual reproduction of my new variety at Aberdeen, Scotland, shows that the aforementioned characteristics come true to form and are established and transmitted through succeeding propagations.

The accompanying drawing shows typical specimens of the growth and flower of my new variety in different stages of development and as depicted in color as nearly true as it is reasonably possible to make the same in color illustration of this character.

The following is a detailed description of my new variety, with color terminology in accordance with the Horticultural Color Chart of the Royal Horticultural Society:

Type: Hardy; tall bush; seedling; for garden decoration.
Class: Hybrid tea.
Propagation: It does hold its distinguishing characteristics through succeeding propagations by grafting budding.

*Flower*

Flowers borne: Singly or two or three or four or five or several to stem; in irregular cluster; on strong, medium to long stems.
Quantity of bloom: Free, outdoors or in greenhouse.
Continuity: Continuous.
Fragrance: Strong; more damask than centifolia.
Bud:
*Peduncle.*—Medium long, medium heavy, erect, medium green, Lettuce Green (861/1), almost smooth, few hairs, green.
*Before calyx breaks.*—Size: Medium to large. Form: Pointed ovoid, without foliaceous appendages on the surface of the bud, with slender, entire, little foliaceous parts extending beyond the tip of the bud one-fourth to one-third or more of its length
*As calyx breaks.*—Color: Oxblood Red (823) shaded Ruby Red (827) and Cardinal Red (822)
*As first petal opens.*—Size: Medium to large. Form: Ovoid. Color: Outside: Oxblood Red (823/3) at base shading gradually to Rose Red (724) near petal tips. Inside: Currant Red (821) with deeper Blood Red (820/1) to Oxblood Red (823) shading. White streak often occurs running from the base up the center of the petal. Opening: It does open up well. It is retarded from opening by cold, wet weather.
Bloom:
*Size when fully open.*—Large, 4 to 6 inches.

*Petalage.*—Very double (many petals, usually with no stamens showing); from 48 to 60 petals; arranged regularly.
*Form.*—High centered at first; becoming cupped; petals remaining at first tightly rolled inward; becoming later at maturity cupped.
Petals: Medium leathery, with inside velvety; outside satiny.
*Shape.*—Outer: It is scallop shaped, with base flat, with one notch (similar in shape to a scallop shell). Intermediate: Obovate. (No teeth or notches.) Inner: Obovate, with one notch (sometimes two or three notches).

This description of a newly opened flower was made from a rose grown in July 1969, at Aberdeen, Scotland.

*Color.*—Outer petal: Outside surface: An even shade of Deep Rose Red (724). Inside surface: Currant Red (821 to 821/1). White streak often occurs running up center of petal from the base. Intermediate petal: Outside surface: Rose Red (724) near base, shading to lighter Rose Red (724/1) near petal tip. Inside surface: Turkey Red (721/1) with Blood Red (820/1) shading Inner petal: Outside surface: Rose Red (724); an even color with little variation. Inside surface: Currant Red (821)

This description was made from a rose that was open for three days outdoors in July 1969, at Aberdeen, Scotland.

*Color.*—Outer petal: Outside surface: Deep Rose Red (724) with Light Oxblood Red (823/3) shading. Inside surface: Oxblood Red (823) to Cardinal Red (822). A little Rose Red (724/3) tinting at the base. White streak often occurs running up center of the petal from the base. Inner petal: Outside surface: Crimson (22/1); an even shade with little variation. Inside surface: Deep Rose Red (724) becoming Rose Red (724/1) at the petal base.
*General color effect.*—Newly opened flower: Vivid Currant Red (821); a white streak may be visible on inside of some outer petals. Rose Red (724) in center of flower near the inner petals have yet to unfold. Three days open: Rose Red (724) with warm Crimson (22) heart as inner petals unfold. The outer petals retain much of their Cardinal Red (822) brilliance at this stage imparting a lively hue to the flower.
*Behavior.*—Drop off cleanly; only in extreme conditions will it tend to fade in hot or dry weather, or spot in cold or wet weather.
*Flower longevity.*—On bush in garden seven days in July, cut roses grown outdoors five days in July; cut roses grown in greenhouse five days in July.

*Reproductive organs*

Stamens: Medium, arranged irregularly about pistils.
Filaments: Many, most with anthers, medium long.
*Color.*—China Rose (024/2).
Anthers: All open at once, medium large (inner ones are a little later than the outer ones).
*Color.*—Straw Yellow (604/1). Seldom an anther fused with a petaloid or a pistil.
Pollen: Moderate to abundant, gold.
Pistils: Medium.
Styles: Uneven, medium long, medium heavy, bunched.
Stigma: Yellow.
Ovaries: All enclosed in receptacle.
Hips: Medium ovoid with inconspicuous neck; moderately smooth; medium fleshy; green.

Sepals: Falling soon; medium long; spear shaped,
Seeds: Medium number; medium size.

*Plant*

Foliage:

*Leaves.*—Compound of five, normal, medium large, leathery, glossy.

*Leaflets.*—Shape: Ovoid, with apex acute; base obtuse; margin serrate. Color: Mature—Upper surface: Ivy Green (0001060/2). Under surface: Sage Green (000861/1). Young—Upper surface: Parsley Green (00962). Under surface: Ery Thrite Red (0027/1).

*Rachis.*—(The supporting stem of the compound leaf) Medium heavy. Upper side: Smooth. Under side: Moderately prickly.

*Stipules.*—Medium long, medium wide; medium points; turning out at an angle of more than 45°.

*Disease.*—Resistant to mildew and blackspot.

Growth:

*Habit.*—Bushy, much branched.

*Growth.*—Vigorous.

*Canes.*—Moderately heavy.

*Main stems.*—Bright. Color: Parsely Green (00962/3). Prickles: Many. Color: Brownish Red. Hairs: None.

*Branches.*—Bright. Color: Parsely Green (00962/1). Prickles: Several. Color: Oxblood Red (00823/3). Hairs: None.

*New Shoots.*—Bright. Color: Oxblood Red (00823/2). Prickles: Several. Color: Oxblood Red (00823/2). Hairs: None.

I claim:

1. A new and distinct variety of rose plant of the Hybrid Tea class, substantially as herein shown and descirbed, characterized particularly as to novelty by the unique combination of the red colors, with a very strong fragrance, stiff flower stems, large flower size, high centered form up to the time of maturity, and glossy foliage.

No references cited.

ROBERT E. BAGWILL, Primary Examiner